(12) United States Patent
Iustin et al.

(10) Patent No.: US 9,526,916 B2
(45) Date of Patent: Dec. 27, 2016

(54) ELECTRODE

(75) Inventors: Roman Iustin, Mölndal (SE); Johan Linder, Göteborg (SE); Kjell Westerlund, Uppsala (SE)

(73) Assignee: MICROPOS MEDICAL AB, Gothenburg (SE)

( * ) Notice: Subject to any disclaimer, the term of this patent is extended or adjusted under 35 U.S.C. 154(b) by 1251 days.

(21) Appl. No.: 13/256,829

(22) PCT Filed: Mar. 16, 2010

(86) PCT No.: PCT/EP2010/053379
§ 371 (c)(1),
(2), (4) Date: Sep. 15, 2011

(87) PCT Pub. No.: WO2010/106062
PCT Pub. Date: Sep. 23, 2010

(65) Prior Publication Data
US 2012/0016229 A1 Jan. 19, 2012

(30) Foreign Application Priority Data
Mar. 16, 2009 (SE) ...................... 0900340

(51) Int. Cl.
*A61B 5/05* (2006.01)
*A61B 5/04* (2006.01)
(Continued)

(52) U.S. Cl.
CPC ........... *A61N 5/1048* (2013.01); *A61B 5/0002* (2013.01); *A61B 5/06* (2013.01); *A61B 5/061* (2013.01);
(Continued)

(58) Field of Classification Search
CPC ......... A61B 6/42; A61B 6/4208; A61B 6/425; A61B 6/4258; A61B 6/4494; A61B 6/54; A61B 6/547; A61B 6/548; A61B 5/06; A61B 5/061; A61B 5/065
(Continued)

(56) References Cited

U.S. PATENT DOCUMENTS 4,001,830 A * 1/1977 Ishimaru et al. ............. 343/702
4,484,076 A * 11/1984 Thomson .................. 250/370.07
(Continued)

FOREIGN PATENT DOCUMENTS

WO WO 2007/061351 A1 5/2007
WO WO 2009/015104 A2 1/2009

*Primary Examiner* — Thomas J Sweet
*Assistant Examiner* — William Chou
(74) *Attorney, Agent, or Firm* — Birch, Stewart, Kolasch & Birch, LLP

(57) ABSTRACT

The present invention relates to an electrode configured to be fixable relative to a target area within a body, the electrode comprises: a positioning device for tracking variations of a position of the electrode relative to a radiation source, a dose measuring unit to detect administered dose in the target area from the radiation source, and an identification unit. The identification unit and the dose measuring unit are configured to be connectable to an externally arranged control unit via a first pair of electrical connections. The identification unit comprises: an electronic identification tag, and a switch configured to alternate between a first mode in which administered dose from the radiation source may be detected in the dose measuring unit, and a second mode in which the identification tag may be read by the externally arranged control unit.

17 Claims, 2 Drawing Sheets

(51) Int. Cl.
 *A61B 6/00* (2006.01)
 *A61N 5/10* (2006.01)
 A61B 5/06 (2006.01)
 A61B 5/00 (2006.01)
(52) U.S. Cl.
 CPC ............... *A61B 5/065* (2013.01); *A61B 6/42* (2013.01); *A61B 6/425* (2013.01); *A61B 6/4208* (2013.01); *A61B 6/4258* (2013.01); *A61B 6/4494* (2013.01); *A61B 6/54* (2013.01); *A61B 6/547* (2013.01); *A61B 6/548* (2013.01)
(58) Field of Classification Search
 USPC ....... 600/372, 107, 412, 414, 424, 436, 474; 250/370.07, 363.04, 358.1, 252.1
 See application file for complete search history.

(56) References Cited

U.S. PATENT DOCUMENTS

| | | | |
|---|---|---|---|
| 6,398,710 B1 | 6/2002 | Ishikawa et al. | |
| 2003/0040670 A1* | 2/2003 | Govari | 600/424 |
| 2003/0137320 A1* | 7/2003 | Grundl | H02M 7/003 326/1 |
| 2008/0188825 A1* | 8/2008 | Atanasoska et al. | 604/509 |
| 2008/0230705 A1* | 9/2008 | Rousso et al. | 250/363.04 |
| 2008/0292054 A1* | 11/2008 | Rosengren et al. | 378/96 |

* cited by examiner

ELECTRODE

TECHNICAL FIELD

The present invention relates to an implantable electrode suitable for medical applications.

BACKGROUND

During radiotherapy it is essential to track the movement of the target area in order to increase the efficiency of the treatment and to reduce the effect of radiation on nearby tissue. Positioning systems have been developed by Micropos Medical AB to track variations using an emitted electromagnetic signal which is received by a plurality of receiving elements, as disclosed in the published international application WO 2005/104976.

In the published international application WO 2007/061351, assigned to Micropos Medical AB, a combined device for dose measurement and tracking positioning is disclosed. Other types of sensors, such as temperature, are also suggested to be implemented together with an electronic identification tag used to verify the patient before performing radio therapy treatment.

A drawback with the prior art devices is that the design is rather complex which results in an expensive or bulky design.

SUMMARY OF THE INVENTION

An object with the present invention is to provide an implantable electrode adapted to be used for positioning that also can measure administered dose from a radiation source, as well as verify the identity of the patient, that has a simplified structure compared to prior art electrodes.

This object is achieved by an implantable electrode having a positioning device for tracking variations of a position of the electrode relative to a radiation source. A combined dose measuring unit and identification unit is connected between a first pair of electrical connections, preferably provided in a shielded multi wire cable, to an externally arranged control unit. The identification unit comprises: an electronic identification tag, and a switch configured to alternate between a first mode in which administered dose from the radiation source may be detected in the dose measuring unit, and a second mode in which the identification tag may be read by the externally arranged control unit.

An advantage with the present invention is that only a pair of electrical connections is needed to measure an administered dose from a radiation source and to determine an electronic identity of the electrode. This will result in a simplified structure which is easier to manufacture compared to prior art electrodes.

In a preferred embodiment, the positioning device is an antenna element connected to the externally arranged control unit via a second pair of electrical connections, preferably provided in the shielded multi wire cable.

An advantage with a preferred embodiment of the present invention is that only two pairs of electrical connections in a cable (e.g. three wires and the shield, or four wires without the shield) are needed to control the electromagnetic antenna structure, which is used to determine the position of the electrode when implanted within a body, and to measure administered dose from a radiation source and to verify the identity of the electrode and thus the body.

An advantage with a preferred embodiment is that the ambient temperature of the electrode when implanted in a target area may be determined without the need of a separate temperature sensor.

Further objects and advantages may be found by a skilled person in the art from the detailed description.

BRIEF DESCRIPTION OF DRAWINGS

The invention will be described in connection with the following drawings that are provided as non-limited examples, in which.

DETAILED DESCRIPTION

Figure 1:
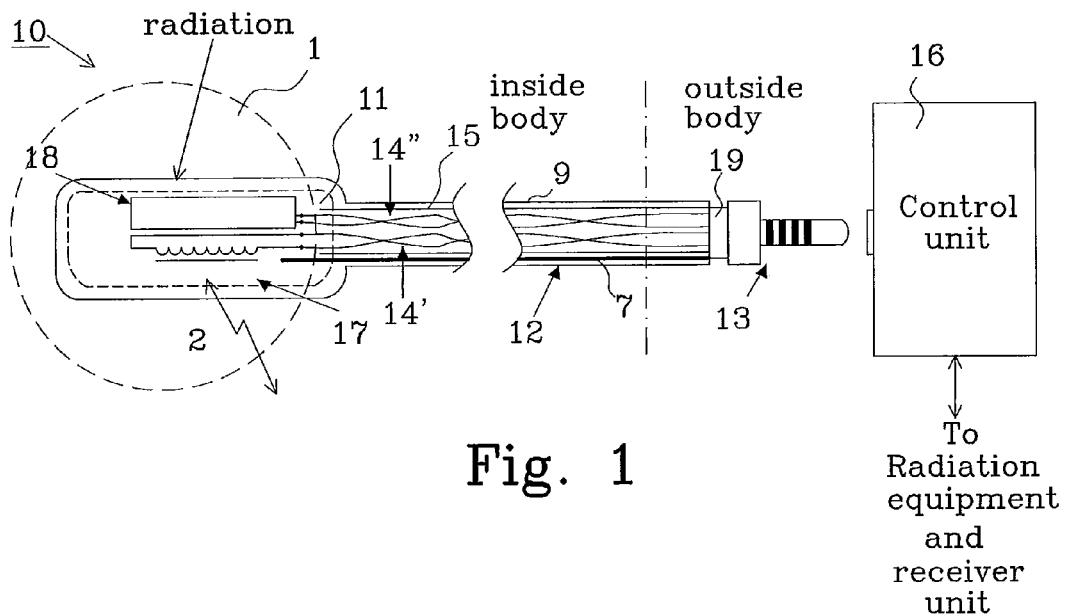
FIG. 1 shows a first embodiment of an electrode according to the invention.

FIG. 1 describes a first embodiment of an electrode 10, preferably an implantable electrode, suitable for medical applications. The electrode 10 comprises a main unit 11 arranged at a first end of a multi wire cable 12 and a connector 13 arranged at a second end of the multi wire cable 12. The multi wire cable 12 comprises in this embodiment of two pairs of electrical connections (such as twisted pair wires) 14' and 14" within a shield 15, which interconnects the connector 13 with the main unit 11. An explant line 7, e.g. an aramid fibre (aromatic polyamide), having a tensile strength over 100 Newton (>100N) is preferably arranged beside the cable 12 and connected between the main unit 11 and the connector 13 to facilitate the removal of the main unit 11 from a target area 1. A biocompatible cover 9 is preferably arranged over the explant line 7, the cable 12 and the main unit 11 to avoid any problems that could occur when the electrode 10 is partly positioned within a body as indicated by the dash-dotted line.

The main unit 11 comprises an antenna element 17, e.g. implemented as a coil on a ferrite rod, configured to transmit an electromagnetic signal 2 adapted to be received in a receiving unit (not shown) to track variations of a position of the electrode relative a radiation source (not shown). The antenna element 17 is connected over one pair of electrical connections, i.e. the wires of a first of the twisted pair wire, 14'. It is also possible to track variations of the position of the electrode by receiving multiple electromagnetic signals 2 in the antenna element 17 originating from a plurality of external antenna elements in the external antenna unit (not shown). The explant line 7 is preferably attached to the ferrite rod of the antenna element 17.

The main unit 11 is fixable relative the target area 1 within a body and the radiation source emits radiation into the target area 1. In order to monitor the administered dose in the target area from the radiation source, the main unit 11 is also equipped with a dose measuring unit 18, which in this embodiment is connected over another pair of electrical connections, i.e. the wires of a second twisted pair wire, 14" and an identification unit 19 positioned at the connector 13. The shield 15 of the multi wire cable 12 is only used for shielding in this embodiment.

The connector 13 is configured to be connected to an external control unit 16, which in turn is in communication with the radiation equipment and the external antenna unit. It should be noted that the connector 13 is configured to be arranged outside the body when the main unit 11 is fixated in relation to the target area.

The control unit 16 is configured to verify the identification of the implant (and thereby the patient since the implant is fixated to the patient during the complete radiotherapy treatment process) and thereafter measure administered dose from a radiation source. The dose measuring and identification unit is described in more detail in connection with FIG. 4. If the antenna element 17 is configured to transmit the electromagnetic signal, the control unit also generates and controls the electromagnetic signal 2 which is transmitted from the antenna element 17 and thereafter is received by a plurality of receiving elements in the external antenna unit (not shown). On the other hand, if the antenna element 17 in the electrode is configured to receive multiple electromagnetic signals 2, the control unit generates and controls the multiple electromagnetic signals transmitted from the external antenna unit.

Furthermore, the antenna element 17 has an internal resistance indicative of surrounding temperature in the target area 1, and the externally arranged control unit 16 may monitor the surrounding temperature of the target area 1 by measuring the internal resistance. The temperature dependency of the antenna element is calibrated by measuring the internal resistance at two specific temperatures, e.g. at 22° C. (room temperature) and at 37° C. (in the target area 1 before radiotherapy commences). The internal resistance may be measured at the same time as the electromagnetic signal(s) is/are transmitted, or received, in the antenna element 17.

The dose measuring unit 18 and the identification unit 19 will operate in two modes, a first mode in which the radiation from the radiation source will create a DC current measured by the control unit 16, and a second mode in which the control unit verifies the identity from the identification unit 19. This process is described in more detail in connection with FIG. 4.

Figure 2:
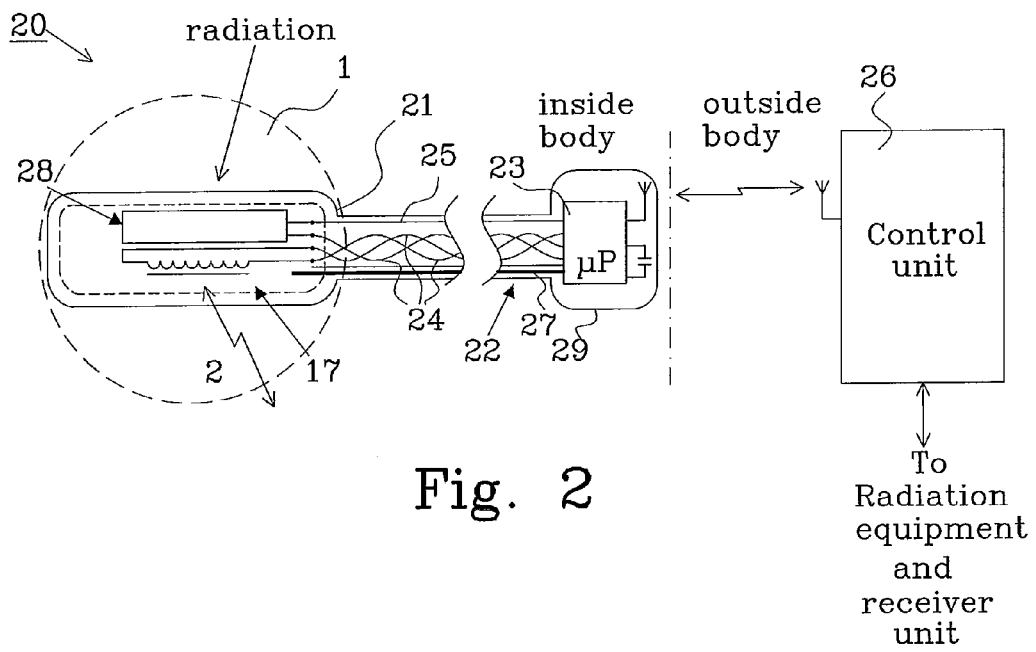
FIG. 2 shows a second embodiment of an electrode according to the invention.

FIG. 2 shows a second embodiment of an electrode 20. A shielded multi wire cable 22, having only three twisted wires 24 and a shield 25, is connected between a processing unit 23 and a main unit 21. An aramid line 27 having a tensile strength over 100 Newton (>100N) is preferably arranged beside the cable 22 and connected between the main unit 21 and the processing unit 23 to facilitate the removal of the main unit 21 from a target area 1. The complete electrode 20, i.e. the explant line 27, the main unit 21, the cable 22 and the processing unit 23, is preferably provided with a biocompatible cover 29 since it is configured to be arranged within a body during use.

The antenna element 17, similar to the antenna element used in FIG. 1, is connected over one pair of electrical connections, i.e. a first and a second of the wires 24, and a dose measuring unit 28 is arranged in the main unit 21 and is connected between another pair of electrical connections, i.e. a third of the wires 24 and the shield 25. An electronic identification tag is arranged in the processing unit 23. The processing unit 23 communicates wirelessly with an external control unit 26, which in turn is connected to the radiation equipment and an external antenna unit (not shown). Furthermore, the processing unit 23 is provided with a microprocessor µP configured to switch between the first and second mode of operation, as well as measure the DC current during the first mode of operation and to provide the identity to the external control unit 26 during the second mode of operation.

The process of determining the administered dose from the measured DC current may be implemented either in the processing unit 23 or in the control unit 26, and the verification of the identity is performed in the control unit 26. The control unit 26 preferably instructs the processing unit 23 to switch between the different modes of operation since it also controls the process of the radiation equipment. The internal resistance of the antenna element 17 is measured by the processing unit 23, but the process of determining the temperature in the target area 1, based on the calibration as explained above, is preferably performed in the control unit 26.

The purpose of the capacitor attached to the processing unit 23 is to store energy provided from the control unit 26. In an alternative configuration, a battery is provided within the processing unit 23.

Figure 3:
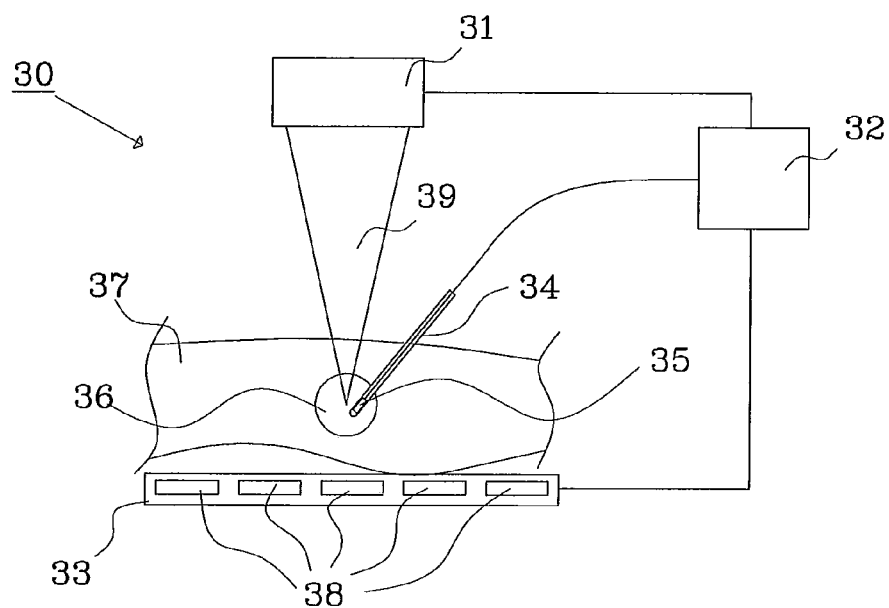
FIG. 3 shows a radiotherapy system provided with an electrode according to the invention.

FIG. 3 shows a system 30 for performing radiotherapy using radiation equipment 31 with a radiation source, a control unit 32, an external antenna unit 33 and an electrode 34 as described in connection with FIG. 1. The control unit 32 is connected to the radiation equipment 31, the external antenna unit 33 and also communicates with the electrode by wires (or alternatively through a wireless connection if an electrode as described in connection with FIG. 2 is used).

The electrode 34 comprises a main unit 35 where the antenna element for tracking variations in position and the dose measuring unit are situated, and the main unit 35 is fixated in relation to a target area 36 within a body 37. The identification unit (not shown) is arranged outside the target area 36 as described in connection with FIGS. 1 and 2. The external antenna unit 33 comprises a plurality of external antenna elements 38, which are used to track the antenna element in the electrode 34. The control unit 32 is also configured to keep track of the distance between the external antenna elements 38 in the external antenna unit 33 and the radiation source in the radiation equipment 31 in order to control the radiation beam 39, as well as to monitor the temperature in the target area 36 by measuring the internal resistance of the antenna element arranged in the main unit 35.

Figure 4:
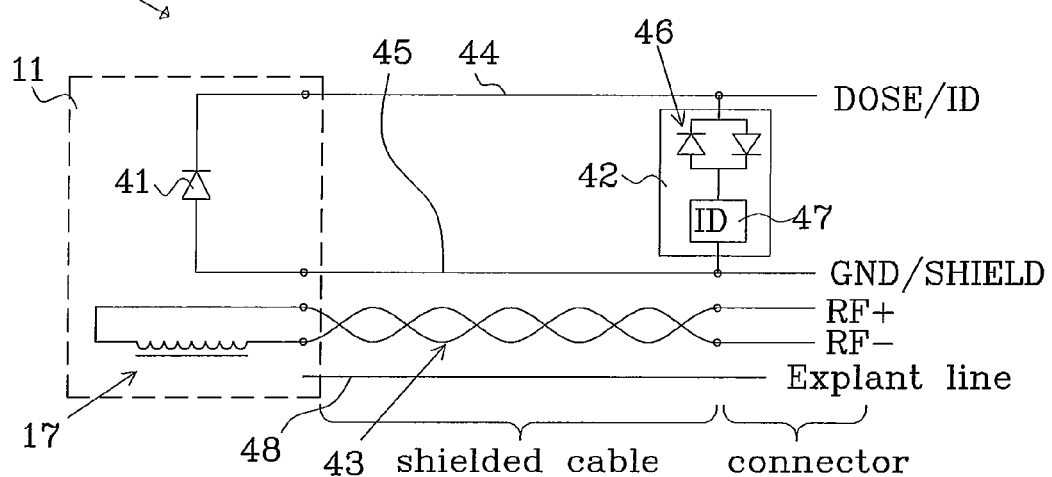
FIG. 4 shows a detailed view of a main unit in an electrode as described in FIG. 1 with a preferred implementation of the dose/ID unit.

FIG. 4 shows a detailed view of an electrode 40 similar to the electrode described in connection with FIG. 1 comprising a dose measuring unit 41 and an antenna element 17 arranged within the main unit 11, and an identification unit 42 arranged at the connector (not shown). The antenna element 17 preferably comprises a coil on a ferrite rod and is connected to one pair of electrical connections, such as a twisted pair wire 43 (marked RF− and RF+ in the connector), to transfer an electromagnetic RF signal between a control unit (not shown) and the antenna element 17 as described above in connection with FIGS. 1 and 2. The internal resistance of the antenna element 17 is also measured over the twisted pair wire 43.

The dose measuring unit 41 comprises a diode, which is connected to another pair of electrical connections, in this embodiment between a single wire 44 (marked DOSE/ID) and ground 45 (marked GND/SHIELD), and the identification unit 42 comprises a switch 46 implemented as a bridge of two Schottky diodes, in series with an electronic identification tag 47, preferably implemented in a chip. The identification unit 42 is connected parallel with the dose measuring unit 41 at the connector side of the shielded cable. In FIG. 1, the dose measuring unit 18 is connected to a second twisted pair wire 14" instead of using the available shield 15 and one wire of the twisted pair.

The switch 46 makes it possible to switch between the two modes of operation, as described above. The first mode, i.e.

dose measuring mode, is achieved when zero volt DC is applied between the single wire 44 and ground 45, and the second mode, i.e. the identification mode, is achieved when a DC voltage is applied over the measuring diode 41 to arrange the diode 41 in reverse, e.g. by applying five volts reverse DC between the single wire 44 and ground 45.

First Mode (Dose Measuring Mode)

When zero volts DC (0 $V_{DC}$) is applied between the single wire 44 and ground 45, the switch is closed since a Schottky diode requires at least 0.4 volts to conduct current. A DC current may thereafter be measured over the diode 41, which is proportional to the exposed amount of radiation but calibration is needed to determine the administered dose in the target area.

Second Mode (Identification Mode)

When a voltage of five volts DC (+5 $V_{DC}$) is applied between the single wire 44 and ground 45, the switch 46 is open and the diode 41 is in reverse. The electronic identification tag 47 may thereafter be read by the control unit.

The control unit may also comprise an integrator that integrates the measured DC current during the first mode of operation, and the administered dose may be determined when a dose calibration factor (which is determined during calibration for each diode) is taken into account.

A memory used for storing necessary patient data, dose calibration data, etc may be implemented in the identification unit 42, or in the external control unit to which the electrode 40 is intended to be connected.

An aromatic polyamide, such as Kevlar or Vectran, is preferably included as an explant line 48 in the electrode 40, as described above, wherein the explant line 48 connects the antenna element 17 together with the shielded cable to the connector. It is also possible to integrate the explant line 48 in the shielded multi wire cable.

In the above described embodiments, a wire connected antenna element 17 has been used to illustrate a positioning device used for tracking variations of a position of the electrode relative to a radiation source. However, other types of positioning devices, e.g. magnetically induced positioning devices, wireless positioning devices, gold markers, etc., may be used.

It should be noted that the antenna element 17 may be used to heat the tissue in the target area by increasing the power of the transmitted signal, and the temperature in the target area may be monitored at the same time by measuring the internal resistance of the antenna element. Suitable frequencies that may be used to heat the tissue is in the microwave range, such as 980 MHz-2.4 GHz.

It should be noted that although FIGS. 1-4 discloses an implantable electrode, the electrode may be used for breast cancer treatment by attaching the electrode to the surface of the breast.

The invention claimed is:

1. An electrode connectable to a control unit configured to be fixable relative to a target area within a body, said electrode comprising:
   a positioning device for tracking variations of a position of the electrode relative to a radiation source;
   a dose measuring unit to detect administered dose in the target area from the radiation source; and
   an identification unit,
   wherein the identification unit and the dose measuring unit are connected in parallel via only a first pair of electrical connections in a shielded cable for connecting to the control unit to facilitate monitoring radiation dose, and are configured to be communicatively connectable to an externally arranged control unit with all information from both the identification unit and dose measuring unit passing through the first pair of electrical connections, and
   wherein said identification unit comprises:
      an electronic identification tag, and
      a switch configured to alternate between a first mode in which an administered dose from said radiation source may be detected in the dose measuring unit, and a second mode in which the electronic identification tag may be read by the externally arranged control unit, and
   wherein the electronic identification tag is connected to the dose measuring unit via the first pair of electrical connections.

2. The electrode according to claim 1, wherein said switch is controlled by changing an applied DC voltage over the parallel connected dose measuring unit and identification unit.

3. The electrode according to any of claims 1-2, wherein said positioning device and dose measuring unit are arranged within a main unit, said dose measuring unit is connected to a first end of said first pair of electrical connections and said identification unit is connected to a second end of said first pair of electrical connections.

4. The electrode according to claim 3, further comprising an explant line having a tensile strength over 100 Newton (>100 N) arranged beside the first pair of electrical connections and connected to the main unit to facilitate the removal of the main unit from the target area.

5. The electrode according to claim 4, wherein the positioning device comprises a coil on a ferrite rod, and the explant line is connected to the ferrite rod of the positioning device.

6. The electrode according to claim 1, wherein said electrode further comprises a connector configured to be arranged outside the body when the electrode is fixated relative to the target area, said first pair of electrical connections being connected to the connector, which is configured to provide the only connection to said externally arranged control unit from the dose measuring unit and identification unit.

7. The electrode according to claim 1, wherein said identification unit is implemented in a processing unit, configured to be arranged inside the body when the electrode is fixated relative to the target area, said first pair of electrical connections is connected between the dose measuring unit and the processing unit, which is configured to wirelessly communicate with the externally arranged control unit.

8. The electrode according to claim 1, wherein the dose measuring unit is a diode.

9. The electrode of claim 8, wherein the diode of the dose measuring unit is a dose measuring diode, and the switch comprises a bridge of two Schottky diodes connected in series with the electronic identification tag.

10. The electrode according to claim 1, wherein said positioning device is an antenna element configured to be connectable to said externally arranged control unit via a second pair of electrical connections, said first pair and second pair of electrical connections are implemented as a cable having at least three wires and a shield.

11. The electrode according to claim 10, wherein said antenna element has an internal resistance indicative of surrounding temperature in the target area, whereby the surrounding temperature may be monitored by measuring the internal resistance.

12. The electrode of claim 1 wherein said electrode interacts with the externally arranged control unit via an electrical or radio wave connection.

13. A method for measuring administered dose and providing an identity related to an electrode fixed relative to a target area within a body, said electrode having a positioning device for tracking variations of a position of the electrode relative to a radiation source, and a dose measuring unit, wherein said electrode further comprises an identification unit connected in parallel to the dose measuring unit via only a first pair of electrical connections in a shielded cable, the identification unit having an electronic identification tag, which is connected to the dose measuring unit via the first pair of electrical connections, and a switch, said method comprising:
- communicatively connecting the parallel connected identification unit and dose measuring unit to an externally arranged control unit only by a communication path employing a single pair of electrical connections, and
- alternating between a first mode in which an administered dose from the radiation source is detected in the dose measuring unit, and a second mode in which the electronic identification tag is read by the externally arranged control unit with all information from both the identification unit and dose measuring unit passing through the first pair of electrical connections.

14. The method according to claim 13, wherein the method further comprises changing an applied DC voltage over the parallel connected dose measuring unit and identification unit to alternate between the first mode and the second mode.

15. The method according to claim 14, wherein the dose measuring unit is a dose measuring
- diode, and the switch comprises a bridge of two Schottky diodes connected in series with the electronic identification tag.

16. The method according to claim 15, wherein the method further comprises applying zero volts DC over the dose measuring diode during the first mode, and applying a DC voltage over the dose measuring diode to arrange the dose measuring diode in reverse during the second mode.

17. The method according to any of claims 13-16, wherein said positioning device is an antenna element and said method further comprises:
- connecting said antenna element to the externally arranged control unit via a second pair of electrical connections, and
- monitoring surrounding temperature in the target area by measuring an internal resistance of the antenna element.

* * * * *